(12) United States Patent
Charvin

(10) Patent No.: US 8,768,480 B2
(45) Date of Patent: Jul. 1, 2014

(54) IMPLANTABLE SUBCUTANEOUS DEVICE

(75) Inventor: Guy Charvin, Antibes (FR)

(73) Assignee: Neurelec, Vallauris (FR)

( * ) Notice: Subject to any disclaimer, the term of this patent is extended or adjusted under 35 U.S.C. 154(b) by 1361 days.

(21) Appl. No.: 12/466,417

(22) Filed: May 15, 2009

(65) Prior Publication Data

US 2009/0287278 A1    Nov. 19, 2009

(30) Foreign Application Priority Data

May 15, 2008    (FR) ...................................... 08 53147

(51) Int. Cl.
*A61N 1/00* (2006.01)

(52) U.S. Cl.
USPC .................................. 607/60; 607/57; 607/61

(58) Field of Classification Search
USPC ............................................. 607/57, 60–62
See application file for complete search history.

(56) References Cited

U.S. PATENT DOCUMENTS

| | | | | |
|---|---|---|---|---|
| 4,736,747 A | * | 4/1988 | Drake | 607/61 |
| 5,105,811 A | * | 4/1992 | Kuzma | 607/57 |
| 6,178,353 B1 | * | 1/2001 | Griffith et al. | 607/61 |
| 6,308,101 B1 | | 10/2001 | Faltys et al. | |
| 7,200,504 B1 | * | 4/2007 | Fister | |
| 8,340,774 B2 | * | 12/2012 | Hochmair et al. | 607/57 |
| 2003/0139782 A1 | * | 7/2003 | Duncan et al. | 607/48 |
| 2005/0004629 A1 | * | 1/2005 | Gibson et al. | 607/60 |
| 2005/0171579 A1 | | 8/2005 | Tasche et al. | |
| 2006/0184212 A1 | | 8/2006 | Faltys et al. | |
| 2007/0255349 A1 | | 11/2007 | Torgerson et al. | |

FOREIGN PATENT DOCUMENTS

| | | |
|---|---|---|
| GB | 2 134 335 A | 8/1984 |
| WO | 2003092326 A1 | 11/2003 |
| WO | 2005110540 A1 | 11/2005 |

OTHER PUBLICATIONS

French Search Report dated Oct. 31, 2008.

* cited by examiner

*Primary Examiner* — Mark W Bockelman
(74) *Attorney, Agent, or Firm* — Birch, Stewart, Kolasch & Birch, LLP

(57) ABSTRACT

Implantable subcutaneous device of biocompatible material that can receive data and energy by electromagnetic coupling with at least one external device is disclosed. The implantable device bears an airtight housing and a magnet that can hold the other external device centered with the implantable device. The housing bears a hollow crown containing at least electronic device(s) and a coil, and a bottom sealing the opening of the crown in an airtight manner. The magnet has dimensions compatible with a central housing formed by the so-called internal wall of the crown and in which it is positioned.

10 Claims, 4 Drawing Sheets

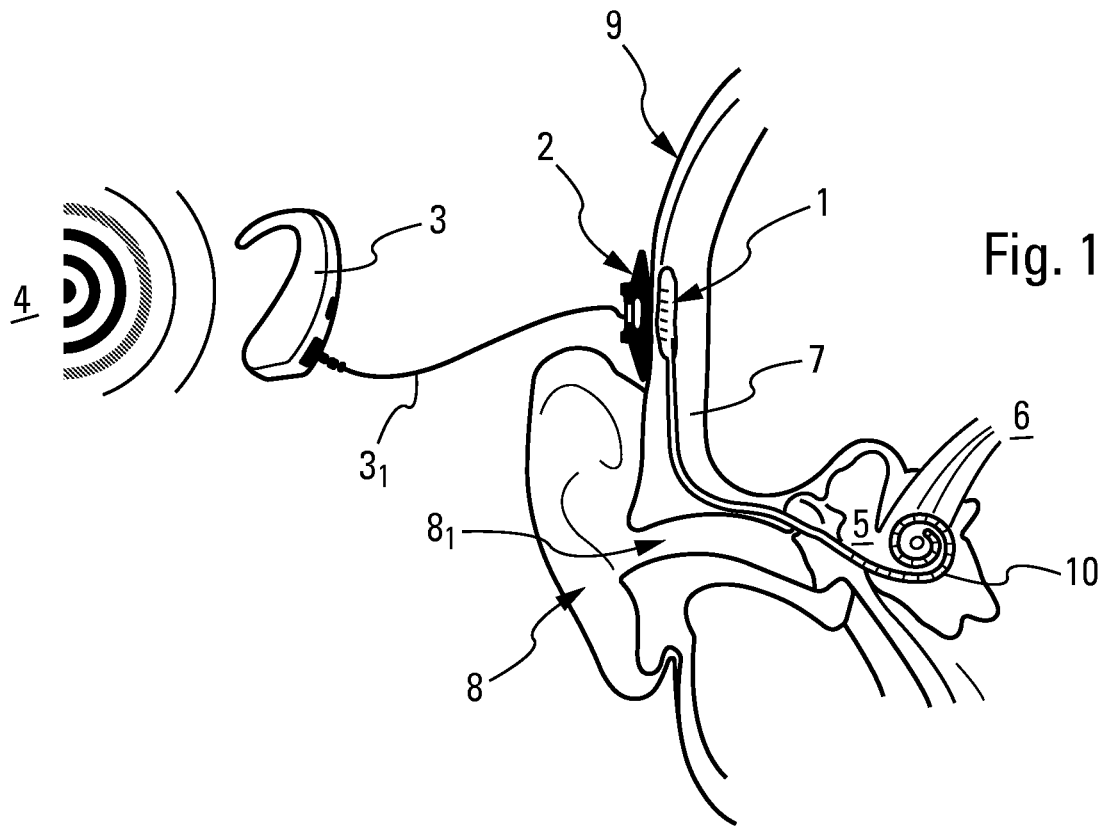
Fig. 1
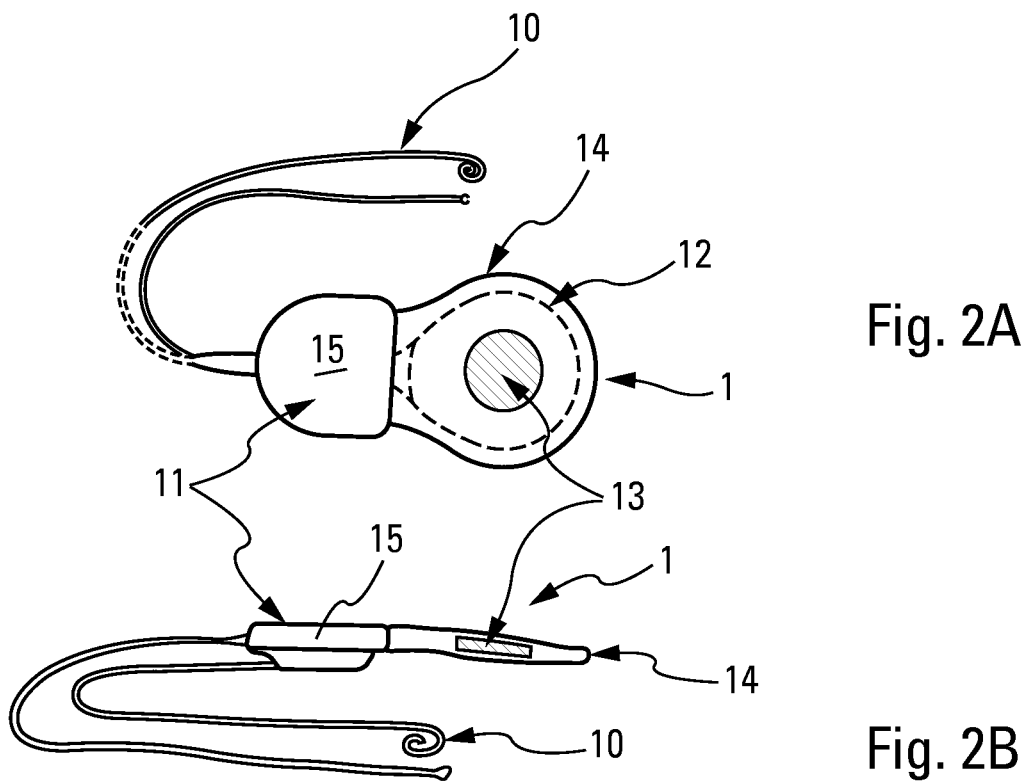
Fig. 2A
Fig. 2B

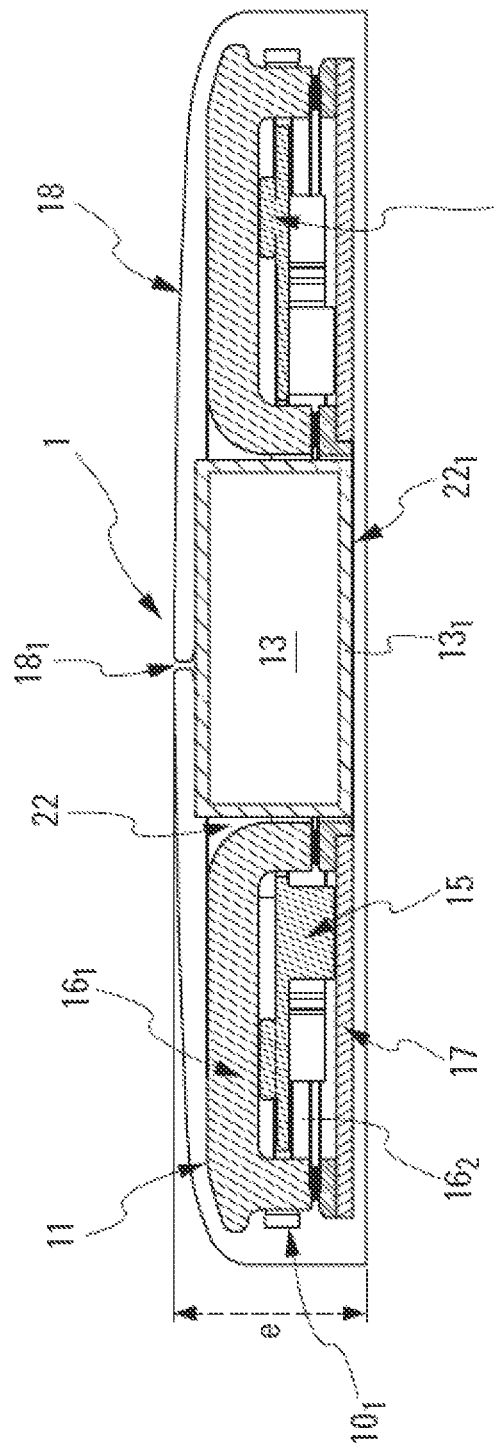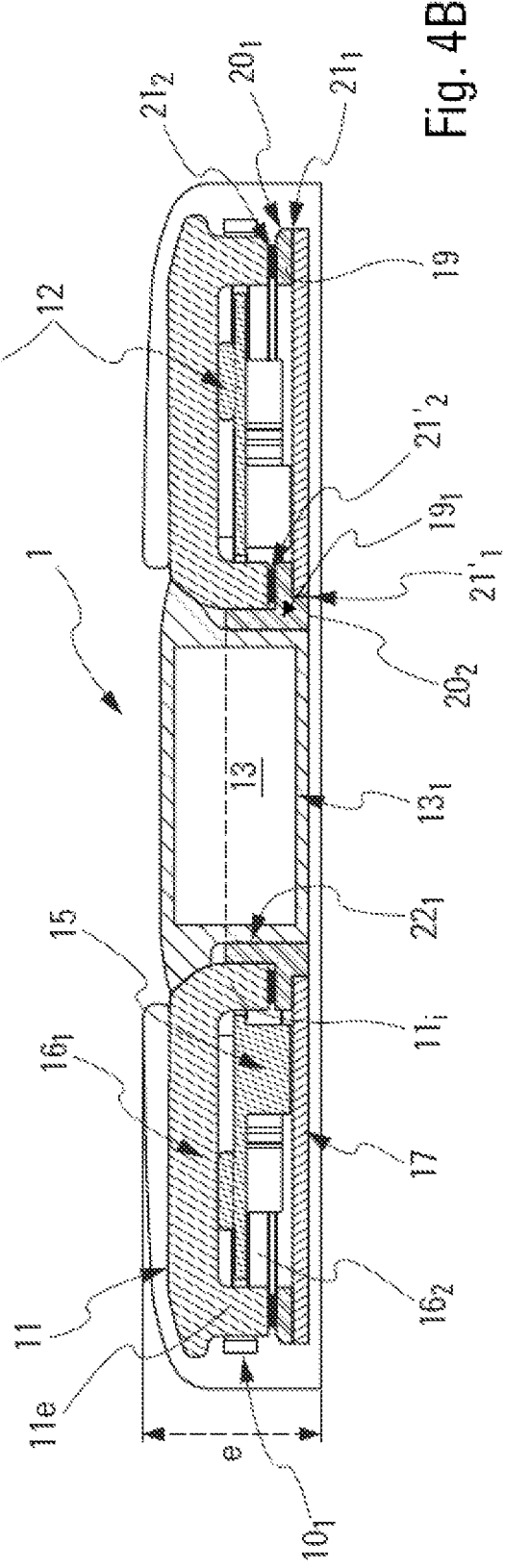

IMPLANTABLE SUBCUTANEOUS DEVICE

BACKGROUND (1) Field of the Invention

The subject of the present invention is an implantable subcutaneous device that can be positioned anywhere in a living body, directly under the skin of this body to send and/or receive data to or from the outside of said body, such as to at least one other device positioned outside said body.

One of the principal applications of this invention is to create auditory prostheses intended to correct profound deafness of a human being and that comprises electrodes for this purpose either implanted in the cochlea, or extracochlear and positioned on the round or oval window of the cochlea, and designed to send electrical signals to the auditory nerve fibers situated in this cochlea.

(2) Prior Art

Such cochlear implants are known and thus replace deficient cochleas, directly stimulating the auditory nerve as a function of sound captured by an external microphone; this microphone is generally situated in a housing also comprising a microprocessor and a support of the behind-the-ear type for positioning it discretely behind and around the ear.

The sounds thus captured by the microphone are digitized and processed in this external housing, which, by means of a set of antennas (at least one of which is associated with this outer housing, and the other, subcutaneous, with the implant) sends information signals corresponding to these sounds to the implant positioned under the skin.

The implant generally comprises a small housing made of titanium and silicone in order to be biocompatible and positioned surgically under the skin; it bears electronic components and receives the information signals from the external antenna by means of its own antenna and for the intracochlear electrode devices sending it to and over these electrodes that have been positioned in the cochlea; like a piano keyboard, each electrode corresponds to a sound signal frequency band and the auditory nerve endings in contact with the electrodes will send the electric impulses to the brain, which will interpret these signals as sound.

Moreover, such an implant requires a minimum energy, which is provided by means of electromagnetic coupling with coils situated face-to-face in the implantable and external devices, respectively, and kept centered with regard to one another by means of a set of magnets (respectively connected to the implantable and external devices); their yield is certainly low since there is no air gap, but it is sufficient for the small quantity of energy required, as long as the various components are chosen and positioned judiciously. Certain implantable devices also have rechargeable batteries.

Other applications are possible, of course, any time that it is necessary or useful to be able to collect data on an organ by using so-called physiological data collection electrodes, or, in contrast, to send information to this organ (such as the cochlea) from the exterior without permanent perforation of the skin.

Various devices are known and developed by different manufacturers, who have filed various patent applications, such as:

patent EP 999 874 of the ADVANCED BIONICS CORPORATION and ALFRED E. MANN FOUNDATION FOR SCIENTIFIC RESEARCH and entitled "Implantable device with improved feed and battery recharge configuration" filed on Jul. 31, 1998, patent application EP 1,166,820 filed by Medtronic, Inc. Entitled "Implantable medical device with an external electric recharging coil" filed on Jun. 19, 2000, or even patent U.S. Pat. No. 6,246,911 of Mr. Peter Seligman filed on Jul. 1, 1999.

All these manufacturers have performed studies and made compromises in the design of their devices in order to simultaneously satisfy contradictory constraints such as: the necessity for the implants to be biocompatible, the simplest possible implementation for the surgeon, a minimum encumbrance, a sufficient yield both in data transmission and in electric recharging of the implant (low yield, in fact, as a result of the proximity of the receiving/transmitting antennas to the titanium housing, and the poor electromagnetic coupling of the coils for energy transfer), as well as the presence of magnets, which also disrupts MRI imaging, and in that one must be able to act on the body of the patient concerned.

Therefore it is necessary, among other things, to maximally reduce the dimensions of the implantable device both in thickness and in surface, while having the possibility of being able to remove the centering magnet without having to remove the implant, in order to be able to do such imaging.

To do this, currently all manufacturers have chosen the compromise of positioning the antenna part and coil of the implant as well as its magnet in a protective silicone casing and positioning this assembly on the side of a titanium housing containing the electronic part and the connection to the cochlear electrodes; the magnet, which is held in place by the silicone casing, which has a opening, can be removed by a small incision once the implant is in place, and the antenna and the coil, offset from the titanium housing, are less disrupted by this housing and permit a satisfactory yield.

The antenna and the coil can either be separate, or made up of a same component that then assures both data transmission and electromagnetic coupling for energy transfer; in the present description, we designate as a coil any component that permits either only electromagnetic coupling for energy transfer, or assuring both, and even possibly at the same time, this function as well as that of a data transmission antenna.

SUMMARY OF THE INVENTION

The present invention permits furthering the research for reducing the encumbrance of the implantable device with increasingly greater resistance, while having good and sufficient characteristics and transmission and electric recharge quality, while allowing the implanted magnetic to be extracted.

For this, a device implantable in the human body, subcutaneous and able to send and/or receive data to or from the outside of said living body and to receive energy by electromagnetic coupling with a coil of an external device, bears, like the currently known devices, at least one coil, a sealed (as airtight, watertight, gastight . . . ) housing containing electronic means at least for stimulation and/or collection and a magnet that can hold and center the coil of said other external device with the one of the implantable device, and it is such that, according to the invention:

said housing has a hollow crown, forming an annular U-shaped groove, made of a biocompatible material that is permeable to electromagnetic waves, containing at least said electronic means and said coil, and a bottom of biocompatible material tightly closing the opening of the hollow part of the crown, said magnet has dimensions compatible with the central housing formed by the so-called inner wall of the crown and open on at least one side, and in which it is positioned.

In preferential embodiments, the magnet is positioned in the central housing in a reversible and extractable manner, and the material of the hollow crown is ceramic, while the material of the bottom is titanium.

In the principal application of the invention, the device comprises at least one external wired electrode, which can therefore be a cochlear electrode, comprising several electrodes and whose distal end can be housed on, against, or in any organ to and/or from which said data are sent and/or collected by the electronic means of the implantable device: this wired electrode and which is connected by its proximal end, preferentially to the radial periphery of the hollow crown of the housing of this implantable device, and preferably at several connection points, each corresponding to a wired electrode.

The result is a new, very compact, implantable subcutaneous device that can have a thickness of at least 5 mm for 30 mm of outer diameter and which limits both its outer surface and the dimensions of the part of the external device that faces it; its positioning is thus facilitated, also reducing the trauma of detaching the skin, and the implant makes fewer shadows during MRI or x-ray imaging; the implantable device also permits, according to the invention, placing the implant magnet nearest the skin, assuring a greater attraction with the external magnet, which permits reducing the strength of these magnets and thus their dimensions, and also reducing the overall size of the assembly of devices.

In addition, making the housing of ceramic offers greater shock resistance, both by the material and the shape of the hollow crown part forming the housing for the electronic part and the coil and which constitutes a U-shaped arch shorter than that of a disk-shaped housing.

Certainly the presence of a titanium bottom, even though it does not constitute a closed Faraday cage like housings made entirely of titanium, degrades the signal transmissions, but the electronic devices that the person skilled in the art can make with his or her current knowledge perform well enough to compensate.

BRIEF DESCRIPTION OF THE DRAWING(S)

The following description refers to the attached drawings, which show non-limiting examples of embodiments of the device according to the invention.

FIG. 1 is a general view of one example of an intracochlear auditory prosthesis that can use a device according to the invention.

FIGS. 2A and 2B are top and profile views, respectively, of an implantable device known in the field of auditory prostheses.

FIGS. 4A, 4B and 4C are sectional views of three embodiments of the sealed housing of an implantable device according to the invention and such as shown in FIG. 3.

DETAILED DESCRIPTION OF THE PREFERRED EMBODIMENT(S)

Figure 3:
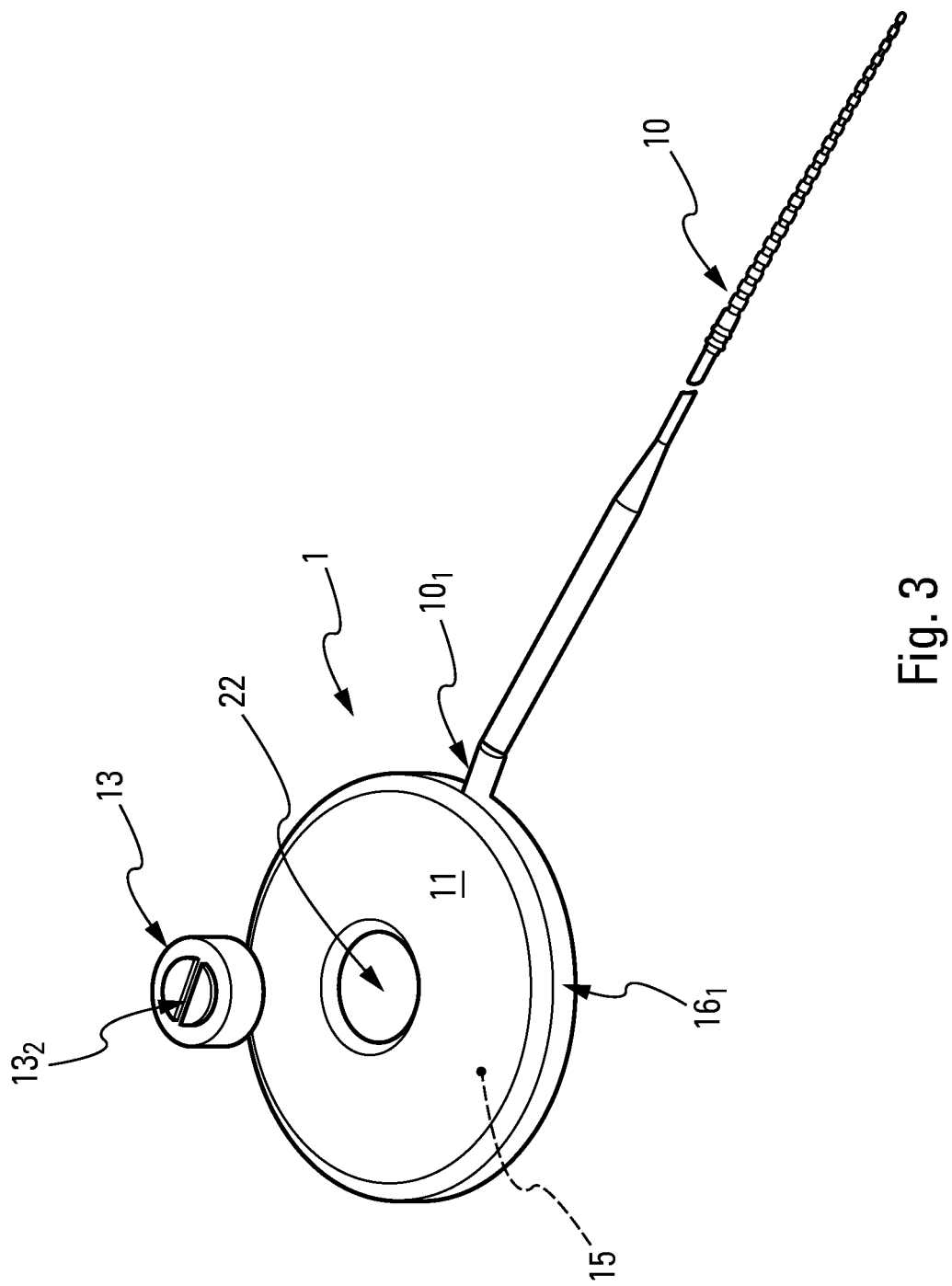
FIG. 3 is a simplified perspective view of a device according to the invention shown as an example in the field of cochlear auditory prostheses with wired electrode.

The entire description of the figures below is only one example of embodiment referring to the principal application of the invention, which is to create auditory prostheses comprising an implantable subcutaneous device, but the device according to the invention can be used in other applications, each time that it is necessary or useful to be able to collect data on an organ by using, for example, so-called physiological data collection electrodes, or, in contrast, to send information to this organ (such as the cochlea, taken as an example below) from outside the living body without permanent perforation of the skin.

In the present example of auditory prostheses, such as shown in FIG. 1, sounds 4 are captured by a microphone situated on an outer housing 3, which also comprises a microprocessor to digitize and process the sound thus captured and which is, in general, a support of the behind-the-ear type for placing it discretely behind ear 8. In another embodiment, said outer housing 3 bearing the microphone can be placed in ear 8 and then have a shape suited to the auditory canal $8_1$.

This external housing 3, either by a small connection cable $3_1$, or by a set of antennas, sends the signals thus processed to a device 2, also called external, which includes at least one coil; this device can make use of an antenna as indicated previously; this will be considered to be the case throughout the following description of one example of embodiment, but in other cases, still remaining within the scope of the present invention, the antenna could be independent of the coil, and even separate from external device 2.

This device is held against the skin 9 facing an implanted device 1 by means of a set of at least two magnets each positioned and connected to one of the devices, implanted device 1 being held against the skull 7.

Said implant 1 thus receives the information signals from external device 2 by means of its own coil/antenna; as indicated above, it can receive these signals from a transmitter/antenna separate from this external device, and even directly from a microphone, which could be autonomous and provided with an antenna, and/or which could itself be implantable and could capture basic data, such as sound originating from outside the body. Electronics 15 of implant 1 distribute these signals to and over electrodes 10 positioned in cochlea 5; the endings of auditory nerve 6 in contact with these electrodes transmit the electric impulses to the brain, which interprets them as sound.

According to a particular embodiment of the invention, external device 2 can bear, in addition to the coil/antenna and the magnet, other elements traditionally contained in outer housing 3, such as a microprocessor, cell or battery, microphone, etc, so that housing 3 is no longer necessary. In this configuration, the patient only wears device 2 simply held on the skin by magnetic attraction to the implanted device.

FIGS. 2A and 2B represent one example of implantable housing 11, according to a configuration such as that currently known; it contains electronics 15, which either send electric impulses to the electrodes to stimulate the auditory nerve, or, in other applications, collect data originating from the electrodes to send them toward external housing 2; these known implant housings are currently arranged next to a support/casing 14 generally made of silicone and which contains coil/antenna 12 and magnet 13 for holding and centering by attraction of the magnet situated in external device 2.

Figure 4C:
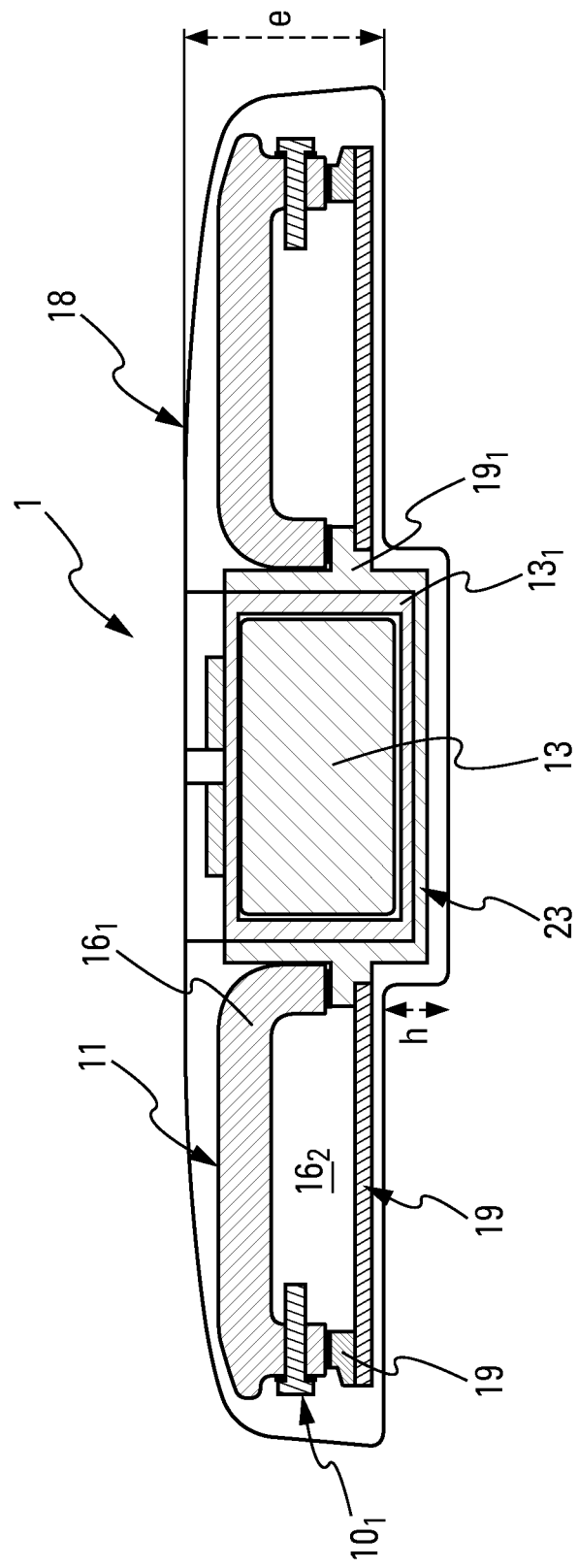

According to the present invention such as shown in FIGS. 3 and 4, housing 11, which contains at least electronic means 15 and said coil/antenna 12 bears a hollow crown $16_1$, forming an annular U-shaped groove that can be clearly distinguished in sectional FIGS. 4A, 4B and 4C, made of a rigid biocompatible material permeable to electromagnetic waves, such as ceramic.

The opening of hollow part $16_2$ of said crown 16 is closed in an airtight manner by a bottom 17 in a biocompatible material, such as titanium.

Implantable device 1 also bears a magnet 13 of compatible dimensions with central housing 22 formed by the so-called internal wall of crown $16_1$ and which is in fact arm $11_i$ of the U shape of the latter orientated toward the center of housing 11, which housing being open on at least one side because it crosses the middle of housing 11, and into which the magnet is introduced, positioned and possibly attached while being extractable such as shown in FIG. 3.

This magnet 13 is then encapsulated in a casing $13_1$ of a rigid biocompatible material such as titanium which, in order to allow fixing the magnet in central housing 22 in a reversible and extractable manner, is either screwed into the cylinder formed by this central housing 22 and endowed with a compatible pitch (as shown in FIG. 4B), or clipped in bottom 17 of housing 11, when said bottom 17 closes not only the opening of hollow part $16_2$ of crown $16_1$ but also that $22_1$ of the corresponding side of housing 22. In this second case, housing 22 is open on both sides.

In the embodiment shown in FIG. 3, magnet 13 bears an opening $13_2$ permitting screwing and unscrewing in a threading created either in housing 22 or in an osteo-integratable titanium insert previously anchored in the bone of the body considered.

In one particular embodiment shown in FIG. 4C, magnet 13 can overshoot bottom 17, opposite the face of the implant that is intended to be orientated toward the outside of the living body, the part of magnet 13, its casing $13_1$ and receptacle 23 of this casing, which receptacle is joined to hollow crown $16_1$ of housing 11, and thus exceeds a height "h" of bottom 17, and is designed to be housed in a cavity drilled beforehand in the bone, such as the temporal bone of the skull for a cochlear implant, of said living body in the desired area. This device permits, on the one hand, reducing the thickness "e" of housing 11, since it is not then connected to that of magnet 13, and the diameter of this magnet, and therefore the surface of the implantable device assembly, and on the other hand to increase the thickness of the implanted magnet, which improves the attraction of the external magnet and thus leads to a better retention of external device 2. This greater magnetic force is perceptible in the configuration described above, where external device 2 has more components, such as the cell and the microprocessor, and is heavier as a result. This device also assures a better hold of the implant due to its mechanical embedding with regard to the bone, and thus reduces the pulling effect generated on the skin by the weight of the assembly.

According to one embodiment shown in FIG. 4A, the biocompatible casing encapsulating magnet 13 is smooth and held in housing 22 by an external casing 18 of flexible biocompatible material permeable to electromagnetic waves such as silicone, which surrounds the entire device and which bears an opening $18_1$ that allows the passage of said magnet 13. This outer casing 18 is not shown in FIG. 3 in order to better show the shape of crown $16_1$ of housing 11 and central housing 22 that can receive magnet 13.

In order to assure a good airtight attachment between bottom 17, preferably titanium, and housing 16 of ceramic, and in order to limit the risk of deterioration of the housing, this titanium bottom 17 is soldered $21_1$ preferably by laser at least on the periphery on a crown 19 also preferably titanium, brazed, preferably with gold, itself $21_2$ previously on the so-called external wall forming the radial periphery of housing 11 of hollow crown $16_1$, (corresponding to arm $11_e$ of the U shape of this housing, turned toward the outside of housing 11); said solder $21_1$ is offset toward the outside and radially in the plane of crown 19 by means of a lip $20_1$ of the latter, with regard to braze $21_2$, which, since it is far from the heating point of solder $21_1$, is not damaged.

A similar assembly is made for the solder of bottom 17 at the inner periphery around housing 22, such as shown in FIG. 4B: solder $21'_1$ of titanium bottom 17 on a crown 19, can be made part of receptacle 23 of magnet 13 as shown in FIG. 4C, is offset toward the outside, and axially perpendicularly to the plane of bottom 17, by means of a lip $20_2$ corresponding to a first arm of said crown $19_1$; a second arm of the crown perpendicular to the first is brazed $21'_2$ onto so-called internal wall $11_i$ of hollow crown $16_1$. Said two arms of this crown $19_1$ thus form an L, as shown in FIG. 4A, but this crown can also form a T, as shown in FIG. 4B, its third arm, also perpendicular to the plane of bottom 17, going up into housing 22 to permit magnet 13 to be screwed by means of respectively compatible thread $22_1$.

The invention claimed is:

1. A device implantable in a living body, subcutaneous and able to send and/or receive data to or from the outside of said body and to receive energy by electromagnetic coupling with a coil of an external device, said implantable device comprising:
    at least one coil;
    a sealed housing containing electronic means at least for stimulation and/or collection;
    an outer casing of flexible biocompatible material permeable to electromagnetic waves, the outer casing completely encapsulating the device; and
    a magnet that can hold and center the coil of said external device with said at least one coil of the implantable device, wherein
    said sealed housing includes
        a hollow crown of biocompatible material and permeable to electromagnetic waves,
    the hollow crown includes
        an external wall forming an external radial periphery of said sealed housing, and
        an internal wall oriented towards a center of said sealed housing,
    the external wall and the internal wall form an opening of an annular U-shaped groove,
    a bottom formed from biocompatible material is attached to an edge of the external wall and to an edge of the internal wall in an airtight manner, tightly closing the opening of the annular U-shaped groove, defining a hollow part of the crown,
    the hollow part of the crown houses at least said electronic means and said at least one coil,
    the internal wall of the hollow crown surrounds a cavity at the center of the sealed housing,
    the cavity is open on at least one side,
    said magnet has dimensions compatible with said cavity and is positioned in said cavity at the center of the sealed housing in a reversible and extractable manner,
    the outer casing includes an opening opposite said cavity at the center of the sealed housing,
    the magnet is encapsulated in a magnet casing made of a biocompatible material, and
    the flexible biocompatible material of the outer casing retains the magnet casing inside said cavity and permits the magnet casing to slide through the opening in response to application of force.

2. The device according to claim 1, wherein
the magnet is encapsulated in a casing of biocompatible material which is screwed into a cylinder formed by said cavity at the center of the sealed housing, and
said casing is endowed with a compatible pitch.

3. The device according to claim 1, wherein
the magnet is encapsulated in a casing of biocompatible material, and
said casing is clipped into the bottom of the sealed housing.

4. The device according to claim 1, wherein
the biocompatible material of the crown permeable to electromagnetic waves is ceramic.

5. The device according to claim 1, wherein
the material of the bottom is titanium.

6. The device according to claim 5, wherein
the titanium bottom is soldered at least on the external periphery on a crown itself and brazed beforehand onto an external wall forming a radial periphery of the hollow crown, said solder being offset by lips with regard to said braze.

7. The device according to claim 1, further comprising
at least one external wired electrode whose distal end can be housed against or in any organ of the living body to which and/or from which data are sent and/or collected by said electronic means.

8. The device according to claim 7, wherein
said at least one external wired electrode is connected by its proximal end to the external radial periphery of the hollow crown of said sealed housing.

9. The device according to claim 7, wherein said wired electrode is a cochlear electrode.

10. The device according to claim 1, wherein
said magnet exceeds the bottom of said sealed housing, opposite a face of the implant intended to be oriented toward the outside of the living body.

* * * * *